United States Patent [19]

Scieszka

[11] Patent Number: 4,633,712
[45] Date of Patent: Jan. 6, 1987

[54] APPARATUS FOR, AND METHOD OF, TESTING AND PULVERIZING PARTICULATE MATERIAL

[75] Inventor: Stanislaw F. Scieszka, Cape Town, South Africa

[73] Assignee: University of Cape Town, Cape Province, South Africa

[21] Appl. No.: 669,860

[22] Filed: Nov. 9, 1984

[30] Foreign Application Priority Data

Nov. 10, 1983 [ZA] South Africa ................ 83/8372

[51] Int. Cl.⁴ .................... G01N 3/58; G01N 3/24
[52] U.S. Cl. ................................. 73/866; 73/7; 73/794; 73/841
[58] Field of Search ............ 73/432 Z, 432 R, 432 K, 73/794, 841, 432 PS, 7, 9

[56] References Cited

U.S. PATENT DOCUMENTS

| | | | |
|---|---|---|---|
| 1,961,333 | 6/1934 | Burns | 73/7 |
| 2,582,223 | 1/1952 | Blackburn et al. | 73/7 |
| 3,915,636 | 10/1975 | Ford, Jr. et al. | 73/432 PS X |
| 4,084,442 | 4/1978 | Kay | 73/432 PS |
| 4,095,461 | 6/1978 | Starita | 73/794 X |
| 4,181,023 | 1/1980 | Clamroth et al. | 73/432 Z |
| 4,196,635 | 4/1980 | Zuber et al. | 73/794 |

FOREIGN PATENT DOCUMENTS

| | | | |
|---|---|---|---|
| 308354 | 8/1971 | U.S.S.R. | 73/432 PS |
| 641328 | 1/1979 | U.S.S.R. | 73/9 |
| 658436 | 4/1979 | U.S.S.R. | 73/7 |
| 673884 | 7/1979 | U.S.S.R. | 73/7 |
| 715965 | 2/1980 | U.S.S.R. | 73/432 Z |
| 903468 | 2/1982 | U.S.S.R. | 73/841 |

OTHER PUBLICATIONS

"Grindability of Coal", Transactions of the American Society of Mechanical Engineers, Fuels Division, 8 pages, Apr. 1931, R. M. Hargrove.

"Installation for the Measurement of the Shear Stresses of Solids at Low Temperatures and High Pressures", Instrum. & Exp. Tech. (USA), vol. 22, No. 1, pp. 266–267, A. A. Zharov et al.

Primary Examiner—Stewart J. Levy
Assistant Examiner—Tom Noland
Attorney, Agent, or Firm—Bernard, Rothwell & Brown

[57] ABSTRACT

Apparatus for determining the mechanical properties of particulate material comprises an outer member defining a cylindrical cavity, and an inner member rotatable in the cavity, the inner and outer members together defining a pulverizing chamber. The inner member has a pressure-bearing face facing the pulverizing chamber and a diametrically disposed groove in which a steel blade can be fitted so as to protrude into the pulverizing chamber. In use, the inner and outer members are rotated with respect to one another, while the particulate material in the pulverizing chamber is placed under axial compression. The torque transmitted from one member to the other, as well as the axial force transmitted from one member to the other is measured during the relative rotation, and these measurements used to determine the mechanical properties of the coal as well as the wear characteristics of the blade. There is further disclosed apparatus of a similar construction, for pulverizing a particulate material continuously, on a production scale, an auger being provided to feed the particulate material continuously into the pulverizing chamber, and there being an annular gap between the inner and outer members, through which pulverized material can escape.

10 Claims, 5 Drawing Figures

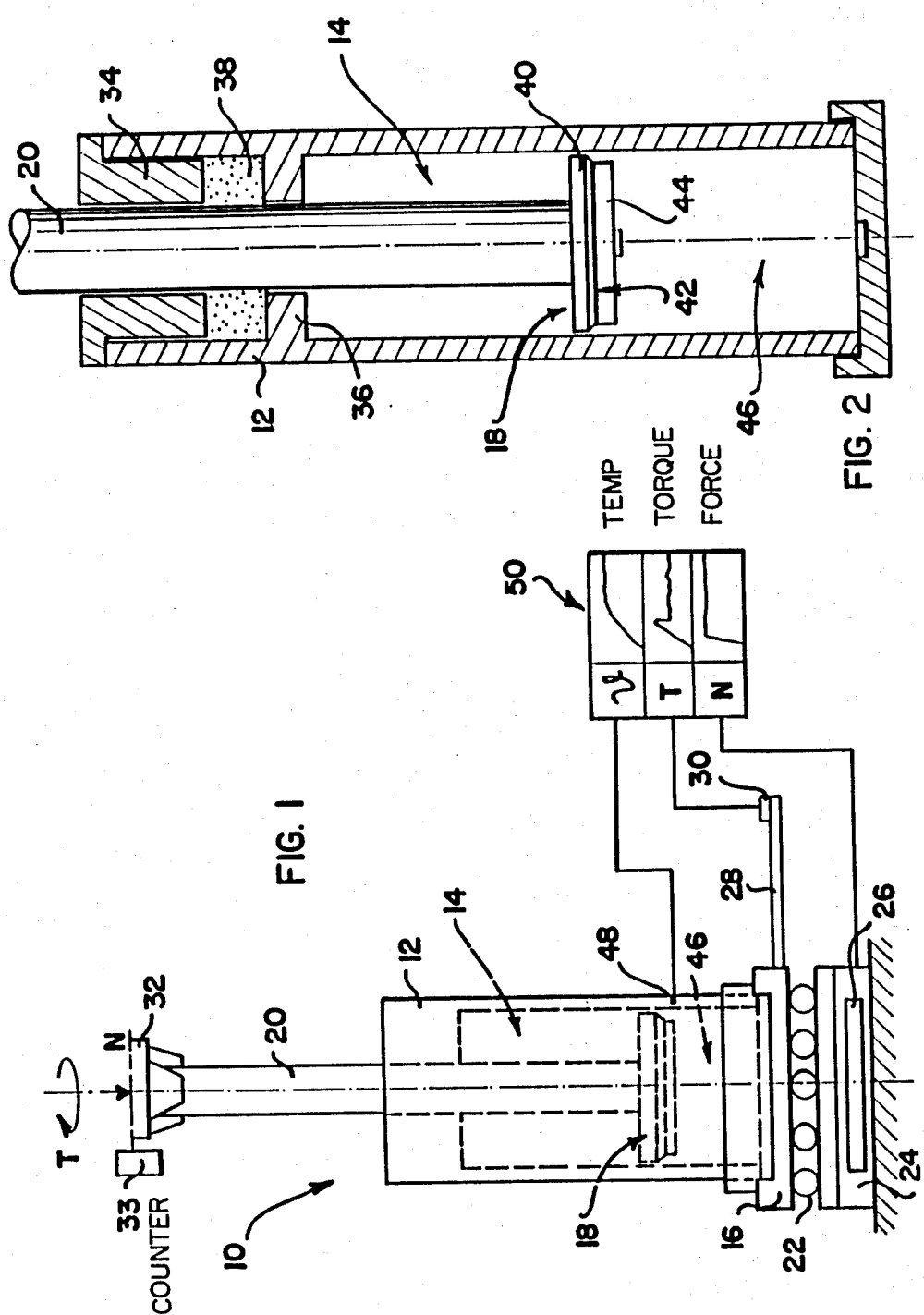

APPARATUS FOR, AND METHOD OF, TESTING AND PULVERIZING PARTICULATE MATERIAL

FIELD OF THE INVENTION

This invention relates to apparatus for pulverizing a particulate material, and for use in determining the mechanical properties of such material. The invention also relates to a method of pulverizing a particulate material and to a method of determining the aforesaid properties.

BACKGROUND TO THE INVENTION

In known methods of determining the mechanical properties of coal, two different instruments are required. One such instrument comprises a pot for containing a sample of the coal to be tested, and a rotor which is rotatable in the pot. The rotor carries sacrificial elements in the form of radially protruding paddles. To test the coal sample, the rotor is rotated in the pot, without axial pressure being applied to the coal sample. The test is referred to as the Yansey-Gear test and yields results from which the abrasiveness of the coal can be determined. The other instrument comprises a plate and steel balls, between which a coal sample is ground. This test yields results from which the grindability (referred to as the Hardgrove index) of the coal can be determined. The results from the first test cannot be used to determine grindability of the coal, nor can the results of the second test be used to determine abrasiveness of the coal.

It is an object of the present invention to provide test apparatus by means of which both abrasiveness and grindability of a particulate material can be determined. It is a further object of the present invention to adapt such apparatus for use in pulverizing a particulate material continuously, on a production scale.

SUMMARY OF THE INVENTION

According to the invention there is provided apparatus for use in determining the mechanical properties of a first, to be pulverized, particulate material with reference to a second material in contact with the first material during pulverization, the apparatus comprising:
  an outer member which has a cylindrical cavity therein;
  an inner member in said cavity, the inner member being rotatable with respect to the outer member about the axis of symmetry of the cavity, the inner and outer members together defining, on one side axially of the inner member, a pulverizing chamber for containing a sample of said first material, the inner member defining a pressure-bearing face facing the pulverizing chamber, whereby the contents of the pulverizing chamber can be placed under axial compression, and the inner member further being adapted to carry a sample element of said second material so as to protrude from the pressure-bearing face into the pulverizing chamber;
  torque measuring means for measuring the torque transmitted from one said member to the other via the contents of the pulverizing chamber during rotation of the members relative to one another; and
  force measuring means for measuring the axial force transmitted from one said member to the other via the contents of the pulverizing chamber during rotation of the members relative to one another.

The pressure-bearing face may be defined by a disc-shaped part having a diametrically disposed groove therein for receiving the sample element.

Preferably, the disc-shaped part is rotatable with little circumferential clearance in the cavity, so that only when particles of the particulate material have been comminuted to less than a predetermined size they can escape from the pulverizing chamber past the inner member.

The apparatus may further comprise counting means for counting the number of revolutions of one said member relative to the other.

The outer member may be supported via a frictionless thrust bearing on a stationary stand, the thrust bearing permitting rotation of the outer member with respect to the stand about said axis of symmetry, and the torque measuring means being arranged to measure the torque tending to rotate the outer member with respect to the stand about said axis of symmetry.

Further according to the invention, there is provided a method of determining the mechanical properties of a to be pulverized particulate material, the method comprising:
  providing apparatus which includes an outer member having a cylindrical cavity therein, and an inner member in said cavity, the inner member being rotatable with respect to the outer member about the axis of symmetry of the cavity, and the inner and outer members together defining, on one side axially of the inner member, a pulverizing chamber;
  placing a sample of said particulate material into the pulverizing chamber;
  rotating the inner and outer members relative to one another while placing the contents of the pulverizing chamber under axial compression;
  measuring the torque transmitted from one said member to the other via the contents of the pulverizing chamber during said relative rotation; and
  measuring the axial force transmitted from one said member to the other via the contents of the pulverizing chamber during said relative rotation.

The particulate material may be coal.

The method may further comprise measuring the degree of comminution which has taken place in the sample as a result of said relative rotation, by removing the sample from the cavity and measuring the amount of particles in the sample having less than a predetermined size.

Still further according to the invention there is provided a method of determining the mechanical properties of a first, to be pulverized, particulate material with reference to a second material in contact with the first material during pulverization, the method comprising:
  providing apparatus which includes an outer member having a cylindrical cavity therein, and an inner member in said cavity, the inner member being rotatable with respect to the outer member about the axis of symmetry of the cavity, and the inner and outer members together defining, on one side axially of the inner member, a pulverizing chamber;
  placing a sample of said first material into the pulverizing chamber;

connecting a sample element of said second material and of known mass to the inner member so as to protrude into the pulverizing chamber;

rotating the inner and outer members relative to one another through a predetermined number of revolutions while placing the contents of the pulverizing chamber under axial compression;

measuring the torque transmitted from one said member to the other via the contents of the pulverizing chamber during said relative rotation; and measuring the axial force transmitted from one said member to the other via the contents of the pulverizing chamber during said relative rotation.

The second material may be steel.

In this aspect the method may further comprise measuring the degree of comminution which has taken place in the sample of particulate material as a result of said relative rotation, by removing the sample of particulate material from the pulverising chamber and measuring the amount of particles in the sample having less than a predetermined size; and measuring the reduction in mass that has taken place in the sample element as a result of said relative rotation.

The invention extends to apparatus for pulverising a particulate material, the apparatus comprising:

an outer member which has a cylindrical cavity therein;

an inner member in said cavity, the inner member being rotatable with respect to the outer member about the axis of symmetry of the cavity, the inner and outer members defining between them an annular gap, and the inner and outer members together defining, on one side axially of the inner member, a pulverizing chamber for containing the particulate material; and means for maintaining the contents of the pulverizing chamber under axial compression during rotation of the inner and outer members with respect to one another, whereby that part of the particulate material present in a first region adjacent the outer member is substantially stationary with respect to the outer member, that part of the particulate material in a second region adjacent the inner member is substantially stationary with respect to the inner member, and that part of the particulate material in an interface region between the first and second regions becomes pulverized and can escape from the pulverizing chamber via said annular gap.

The inner member may have a pressure-bearing face facing the pulverizing chamber, and may comprise a wear-resistant element which protrudes from the pressure-bearing face into the pulverizing cavity.

Said element may be replaceable.

The invention further extends to a method of pulverizing a particulate material, the method comprising:

providing apparatus including an outer member having a cylindrical cavity therein, and an inner member in said cavity, the inner member being rotatable with respect to the outer member about the axis of symmetry of the cavity, the inner and outer members defining between them an annular gap, and the inner and outer members together defining, on one side axially of the inner member, a pulverizing chamber;

feeding the particulate material into the pulverizing chamber; and maintaining the particulate material under axial compression in the pulverizing chamber while rotating the inner and outer members with respect to one another, whereby that part of the particulate material present in a first region adjacent the outer member is substantially stationary with respect to the outer member, that part of the particulate material in a second region adjacent the inner member is substantially stationary with respect to the inner member, and that part of the particulate material in an interface region between the first and second regions becomes pulverized and can escape from the pulverizing chamber via said annular gap.

BRIEF DESCRIPTION OF DRAWINGS

The invention will now be described in more detail, by way of example, with reference to the accompanying drawings.

In the drawings:

FIG. 1 is a schematic diagram of testing apparatus in accordance with the invention, for use in determining the mechanical properties of coal and the wear characteristics of materials used in pulverizing equipment;

FIG. 2 is a vertical section through part of the apparatus of FIG. 1;

DETAILED DESCRIPTION OF PREFERRED EMBODIMENTS

Figure 5:
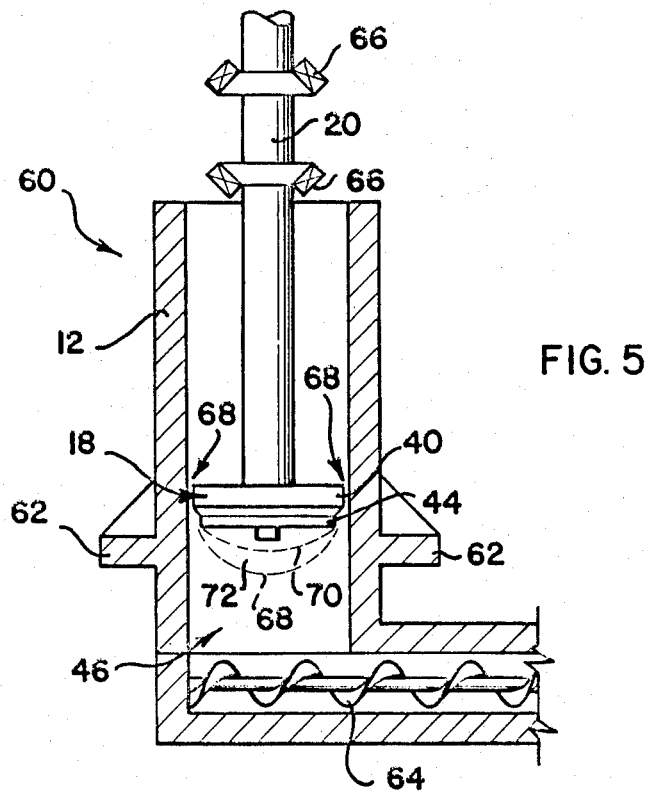
FIG. 5 is a schematic axial section of pulverising apparatus in accordance with the invention, for pulverizing coal or other particulate material continuously, on a production scale.
Figure 3:
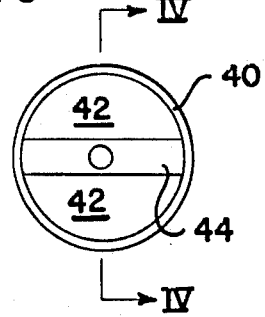
FIG. 3 is a detail under plan of an inner member forming part of the apparatus of FIG. 1.

Referring first to FIGS. 1 and 2, there is shown testing apparatus 10 comprising an outer member 12 having a cylindrical cavity 14 therein and being carried on a support 16, an inner member 18 within the cavity 14, and a vertical shaft 20 which enters the upper end of the cavity 14 and to which the inner member 18 is secured.

The support 16 is carried by a thrust bearing 22 on a stand 24 that incorporates a sensor 26 for sensing the axial or normal force N exerted on the stand. The support 16 has a projecting arm 28 whereby it is connected to a sensor 30 for sensing the torque T tending to rotate the outer member 12 with respect to the stand 24.

The upper end of the shaft 20 is received within the chuck 32 of a drilling machine (not shown) so that a torque T and a vertical force N may be applied to the shaft. The drilling machine is of a kind that is able to operate through a predetermined number of revolutions. A counter 33 for counting the number of revolutions is attached to the drilling machine.

As is illustrated in FIG. 2, the shaft 20 enters the cavity 14 through a brass bearing 34, which is threaded into the upper end of the outer member 12, and is a sliding fit in a locator formed by an internal flange 36 on the chamber wall. A polytetrafluoroethylene seal 38 is located between the inner end of the bearing 34 and the flange 36.

The inner member 18 comprises a disc-shaped part 40 having a downwardly facing pressure-bearing face 42, and a rectangular section blade 44 of carbon steel (conforming to grade 060A15 of BS 970) which protrudes from the pressure-bearing face. The blade 44 is releasably carried on the underside of the part 40. It is slightly shorter than the diameter of the part 40 and is mounted to extend diametrically there-across. The disc 40 has its lower corner chamfered to a smaller diameter portion of the same diameter as the length of the blade 44.

The inner member 18 and the outer member 12 together define, on the side of the pressure-bearing face 42, a pulverizing chamber 46.

In use, the blade 44 is weighed very accurately (conveniently to the nearest 0.0001 g) and then attached to the disc 40. A coal sample is prepared of accurate amount (conveniently 30±0.01 g). The size of the coal in the sample is between 16 to 39 sieve size. The coal sample is placed in the chamber 46. The disc 40 is then inserted into the cavity 14 and the upper end of the shaft 20 mounted in the chuck 32. The inner member 18 is then caused to rotate a predetermined number of times, while downward or normal pressure is applied to the shaft 20.

During rotation of the shaft 20 the torque applied to the coal sample, as transmitted to the outer member 12, is measured, as is the axially compressive force N. The temperature of the chamber is also measured by means of, for example, a thermocouple 48 mounted on the outer member 12 in the vicinity of the chamber 46. The force N, the torque T, and the temperature $\theta$ are recorded on a recorder 50.

The annular gap between the disc-shaped part 40 and the outer member 12 may be selected so that particles which have been comminuted to less than a predetermined size leave the chamber 46 via the gap. In this manner the actual conditions in a production pulverizer are closely simulated.

When the shaft 20 has come to a standstill, the coal sample is removed and sieved (conveniently through a No 200 mesh sieve). The coal passing through the sieve is weighed as is that which remains on the sieve.

Furthermore, the blade 44 is removed from the disc 40, allowed to cool in air to ambient temperature, immersed in industrial methylated spirits and cleaned in an ultrasonic cleaner. It is thereafter dried in a hot-air dryer and allowed to cool, in air, to ambient temperature. It is then re-weighed to the nearest 0.0001 g.

The measurements made above may be used to determine the abrasion factor of coals (AF); the index of comminution (or grindability) of coals (IC); the wear resistance (WR) and relative wear resistance ($\epsilon$) of materials in contact with coal during pulverization; the residual shear strength of crushed coal at a certain stress ($\tau_r$); the apparent cohesion of interlocked coal particles at a certain stress (C); and the ultimate frictional angle of internal resistance ($\phi$).

The above mentioned properties can be defined as follows:

Abrasion factor (AF): The mass of metal lost by abrasion from a carbon steel blade when rotated in a specified mass of coal under specified conditions, expressed in milligrams of metal lost per kilogram of pulverized coal. Only the fraction of coal particles below 75 $\mu$m in size is considered to be pulverized.

Index of comminution (IC): The grindability or ease of pulverization of coals. A prepared sample of coal receives a definite amount of grinding energy (energy input), and the change in size is determined by sieving. The index of comminution (IC) is expressed in milligrams of pulverized coal (fraction below 75 $\mu$m particle size) per Joule of energy input.

Wear resistance (WR): The energy input required to wear the metal blade, when rotated in a specified mass of coal under specified conditions expressed in Megajoules of energy input per gram of metal loss. It will be understood that where the wear resistance of a metal in contact with coal is being calculated, the blade 44 will be made of that metal.

Relative wear resistance ($\epsilon$): The ratio between the wear resistance of the testing material and the wear resistance of the standard material (carbon steel grade 060A15 of BS 970).

Residual shear strength ($\tau_r$): The residual shear strength of crushed coal under a certain normal stress is the resistance that it can offer to shear stress at a given point within itself. When this resistance is reached, continuous shear displacement takes place between the rotating portion of coal and the residual stationary volume.

Mathematically, this can be expressed as follows:

$$\tau_r = [(3T_r)/(2\pi R^3)] \cdot 10^{-6}$$

where
$T_r$ = final residual value of torque, Nm
R = radius of cylindrical chamber, m.

Apparent cohesion (C): The apparent cohesion of interlocked coal particles under a certain stress is the difference between the peak value and the final residual value of the shear strength of the crushed coal. There is a considerable degree of interlocking between the coal particles under a normal stress and before complete shear failure can take place this interlocking must be overcome. In addition, the frictional resistance at the points of contact must also be overcome. After a peak stress is reached at a small value of shear displacement, the degree of interlocking increases and the shear stress necessary to continue the shear displacement is reduced by approximately the value of apparent cohesion. The decrease in the degree of interlocking is caused by the coal particles being crushed and broken up or by the cohesive part of the friction-wear phenomena and by redistribution of the particles (sliding, rolling and lifting).

Mathematically, this can be expressed as follows:

$$C = \frac{3}{2\pi R^3} (T_p - T_r) 10^{-6}$$

where $T_p$ = peak value of torque, Nm.

Ultimate frictional angle of internal resistance ($\phi$):
Mathematically, this can be expressed as follows:

$$\theta = \arctan \frac{\tau r}{\sigma n} = \arctan \frac{3T_r}{2RN}$$

where
$\tau_r$ = final residual value of shear strength, MPa
$\sigma_n$ = normal stress, MPa
N = normal force, N.

Referring now to FIG. 5, reference numeral 60 generally indicates pulverizing apparatus for pulverizing coal on a continuous, production scale. The construction is similar to the testing apparatus illustrated in FIGS. 1 to 4, the same reference numerals being used to designate the same or similar parts.

In the apparatus 60 it is not necessary to carry out the various measurements that are carried out in the apparatus 10. Accordingly, the outer member 12 in FIG. 5 is provided with fixed mountings 62. Coal is continuously fed into the pulverizing chamber 46 by suitable feed means such as, for example, an auger 64, so as to maintain a desired pressure in the pulverizing chamber 46.

The shaft 20 is mounted in thrust bearings 66 and is connected for drive to a motor (not shown).

Between the inner member 18 and the outer member 12 there is an annular gap 68.

In operation, that part of the coal in the chamber 46 which is in the region below the lowermost dotted line 68 remains substantially stationary, whereas that part of the coal above the uppermost dotted line 70 rotates substantially in unison with the inner member 18. In an interface region 72 between the two dotted lines the coal particles rub against one another, causing pulverization. The pulverised coal migrates radially outwardly and upwardly towards the annular gap 68 and those particles that are fine enough pass through the gap into that region of the cavity 14 above the inner member 18. There the pulverised coal is collected for subsequent use. The width of the gap 68 will determine the particle size of the pulverized product.

Figure 4:
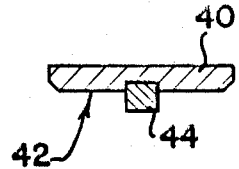
FIG. 4 is a cross-section of the inner member on line IV—IV in FIG. 3.

The blade 44 is replaceable so that, when it has worn, it can readily be replaced. The blade is located in a groove in the pressure-bearing face of the disc 40 which forms part of the inner member 18. It will be appreciated that the blade need not necessarily be of rectangular cross section as illustrated in FIG. 4. It may, for example, be of triangular cross section with one of the apices of the triangle protruding from the pressure-bearing face 42.

I claim:

1. Apparatus for use in determining mechanical properties of a first, to be pulverized, particulate material with reference to a second material in contact with the first material during pulverization, the apparatus comprising:
   an outer member which has a cylindrical cavity therein;
   an inner member in said cavity, the inner member being rotatable with respect to the outer member about the longitudinal axis of symmetry of the cavity, the inner and outer members together defining, on one side axially of the inner member, a pulverizing chamber for containing a sample of said first material, there being a gap between the inner and outer members through which particles of said first material which have been reduced to below a predetermined size can leave the pulverizing chamber, the inner member defining a pressure-bearing face facing the pulverizing chamber, whereby the contents of the pulverizing chamber can be placed under axial compression, and the inner member further being adapted to carry removably a sample element of said second material so as to protrude from the pressure-bearing face into the pulverizing chamber;
   torque measuring means for measuring the torque transmitted from one said chamber to the other via the contents of the pulverizing chamber during rotation of the members relative to one another; and
   force measuring means for measuring the axial force transmitted from one said member to the other via the contents of the pulverizing chamber during rotation of the members relative to one another.

2. Apparatus according to claim 1, wherein said pressure-bearing face is defined by a a disc-shaped part having a diametrically disposed groove therein for receiving the sample element.

3. Apparatus according to claim 1, which further comprises counting means for counting the number of revolutions of one said member relative to the other.

4. Apparatus according to claim 1, wherein the outer member is supported via a frictionless thrust bearing on a stationary stand, the thrust bearing permitting rotation of the outer member with respect to the stand about said axis of symmetry, and the torque measuring means being arranged to measure the torque tending to rotate the outer member with respect to the stand about said axis of symmetry.

5. A method of determining mechanical properties of a to be pulverized particulate material, the method comprising:
   providing apparatus which includes an outer member having a cylindrical cavity therein, and an inner member in said cavity, the inner member being rotatable with respect to the outer member about the longitudinal axis of symmetry of the cavity, there being a gap between the inner and outer members, and the inner and outer members together defining, on one side axially of the inner member, a pulverizing chamber;
   placing a sample of said particulate material into the pulverizing chamber;
   rotating the inner and outer members relative to one another while placing the contents of the pulverizing chamber under axial compression and permitting particles of said particulate material which have been reduced to below a predetermined size to leave the pulverizing chamber through said gap;
   measuring the torque transmitted from one said member to the other via the contents of the pulverizing chamber during said relative rotation; and
   measuring the axial force transmitted from one said member to the other via the contents of the pulverizing chamber during said relative rotation.

6. A method according to claim 5, wherein the particulate material is coal.

7. A method according to claim 5, which further comprises measuring the degree of comminution which has taken place in the sample as a result of said relative rotation, by removing the sample from the cavity and measuring the amount of particles in the sample having less than a predetermined size.

8. A method of determining mechanical properties of a first, to be pulverized particulate material with reference to a second material in contact with the first material during pulverization, the method comprising:
   providing apparatus which includes an outer member having a cylindrical cavity therein, and an inner member in said cavity, the inner member being rotatable with respect to the outer member about the longitudinal axis of symmetry of the cavity, there being a gap between the inner and outer members, and the inner and outer members together defining, on one side axially of the inner member, a pulverizing chamber;
   placing a sample of said first material into the pulverizing chamber;
   connecting a sample element of said second material and of known mass to the inner member so as to protrude into the pulverizing chamber;
   rotating the inner and outer members relative to one another through a predetermined number of revolutions while placing the contents of the pulverizing chamber under axial compression and permitting particles of said first material which have been reduced to below a predetermined size to leave the pulverizing chamber through said gap;

measuring the torque transmitted from one said member to the other via the contents of the pulverizing chamber during said relative rotation; and measuring the axial force transmitted from one said member to the other via the contents of the pulverizing chamber during said relative rotation.

9. A method according to claim 8, wherein said first material is coal and said second material is steel.

10. A method according to claim 8 which further comprises measuring the degree of comminution which has taken place in the sample of particulate material as a result of said relative rotation, by removing the sample of particulate material from the cavity and measuring the amount of particles in the sample having less than a predetermined size; and measuring the reduction in mass that has taken place in the sample element as a result of said relative rotation.

* * * * *